United States Patent [19]

Hajduch

[11] Patent Number: 4,821,720

[45] Date of Patent: Apr. 18, 1989

[54] MEDICAL FASTENING AND CLAMP SYSTEM

[76] Inventor: James D. Hajduch, 1703 Caroline Ave., Whiting, Ind. 46394

[21] Appl. No.: 115,405

[22] Filed: Nov. 2, 1987

Related U.S. Application Data

[62] Division of Ser. No. 637,019, Aug. 2, 1984.

[51] Int. Cl.⁴ .................... A61B 17/12; A61B 17/00
[52] U.S. Cl. ................................. 128/325; 128/346
[58] Field of Search ............. 128/325, 326, 327, 346, 128/133, DIG. 15; 24/509, 508, 500

[56] References Cited

U.S. PATENT DOCUMENTS

| | | | |
|---|---|---|---|
| 821,619 | 1/1897 | Burton | 128/346 |
| 1,615,889 | 2/1927 | Senn | 24/509 |
| 3,203,421 | 8/1965 | Bialick | 128/346 |
| 3,827,107 | 8/1974 | Moore | 128/DIG. 15 |
| 3,884,240 | 5/1975 | Gilman | 128/325 |

*Primary Examiner*—Richard C. Pinkham
*Assistant Examiner*—Benjamin Layno
*Attorney, Agent, or Firm*—Frank J. Uxa, Jr.

[57] ABSTRACT

An improved apparatus for holding tubing, e.g., intravenous tubing, comprises a clamp housing, a holding system to secure the housing in place, and at least one tubing clip secured to the housing and being capable of being opened and closed to accept and hold, respectively, a segment of tubing. In another embodiment, an improved pressure clamp comprises first and second frame portions, a cradle system secured to the second frame portion and being capable of acting to hold a member, e.g., human extremity, on which pressure is to be applied; and a pressure head secured to the first frame portion and being capable of acting to contact the member being held by the cradle system whereby the desired pressure is applied to the member.

11 Claims, 1 Drawing Sheet

U.S. Patent　　　　Apr. 18, 1989　　　　4,821,720
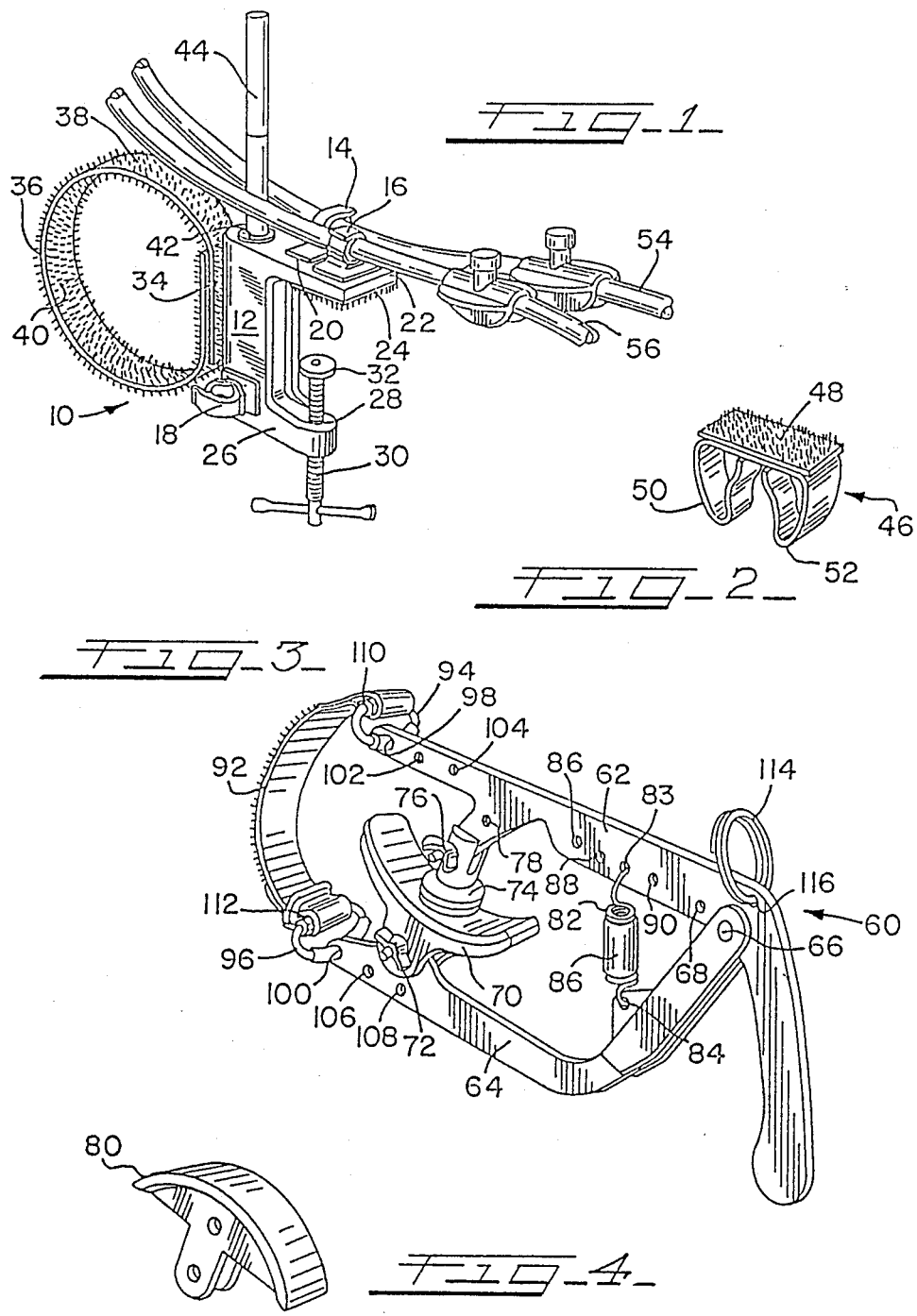

MEDICAL FASTENING AND CLAMP SYSTEM

This application is a division, of application Ser. No. 637,019, filed Aug. 2, 1984.

BACKGROUND AND SUMMARY OF THE INVENTION

This invention relates to an improved clamp apparatus. More particularly, the present invention relates to improved clamps having applicability in the medical and health care industries. This invention may also be used by Veterinarians.

The medical and health care industry is becoming more and more sophisticated. It is often necessary, in order to properly treat patients, to transport fluids via tubing to and from a patient. Intravenous feeding and medication is becoming common place. Kidney dialysis involves repeated transporting of blood from and back to a patient.

Often there are two or more separate lines or tubes being used to treat a single patient. Unless care is taken, those tubes can become tangled and ultimately dislodged from the patient. It would be advantageous to provide a device to hold and orient these separate tubes to reduce the likelihood of these difficulties occurring.

In many situations, a pressure clamp is needed, e. g., to stop or prevent bleeding. Such pressure clamps are often used in conjunction with kidney dialysis.

Also, the clamps do not fit each person's extremities and access artery which vary greatly from individual to individual. The access artery in many instances was located in such a position that clamp placement is tedious, if not impossible. The conventional clamp has no provision for adjustment, rotation, or for locking the clamp to the individual's extremities so as not to fall off if the person fell asleep, was jarred, or has to move at all when the clamp is fastened to the extremity. Tho conventional clamp is also hard to store and have easy access to as it had no provisions for hanging it near the patient for which it was to be used. Clearly, it would be advantageous to provide an improved pressure claim.

An object of the present invention is to provide an improved clamp for applying pressure to a member. Other objects and advantages of the present invention will become apparent hereinafter.

Improved clamp apparatus have now been discovered. In one embodiment, the present invention involves an apparatus useful for holding at least one segment of tubing. This apparatus comprises clamp housing means; clamp holding means associated With the clamp housing means and capable of securing, preferably removeably securing, the housing means in place; and at least one preferably two or more, clip means secured, preferably removeably secured, to the housing means and capable of being quickly opened and closed to accept and hold, respectively, a segment of tubing.

Substantial advantages are obtained with the present tube holding apparatus. For example, this apparatus prevents tubing from tangling; prevents needles from being pulled or jarred from patients; is portable and adaptable; and is easy and relatively inexpensive to manufacture.

In another embodiment, an improved pressure clamp is provided. This clamp comprises a first frame means; a second frame means movably, preferably pivotally, secured to tho first frame means; cradle means secured, preferably adjustably secured, to the second frame means and capable of acting to hold the member, e.g., human extremity, on which pressure is to be applied; and head means secured, preferably adjustably secured, to the first frame means and capable of acting to contact the member being held by the cradle means so that the desired pressure is applied to the member. Preferably, the pressure clamp further comprises a bias means, more preferably spring means, associated with both the first and second frame means and capable of acting to exert a force, more preferably an adjustable force, to maintain the desired pressure on the member.

Among the advantages of the present pressure clamp are durability, economy, balance, to cause less shifting and slippage, better fit and seals to the areas clamped and adjustability.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 1 is a side frontal view, in perspective, of a tube clamp embodiment of the present invention.

FIG. 2 is a side frontal view, in perspective, of a bed rail clamp suitable for use with the tube clamp shown in FIG. 1

FIG. 3 is a side frontal view, in perspective, of a pressure clamp embodiment of the present invention.

FIG. 4 is a side frontal view, in perspective, of an alternate head element suitable for use with the pressure clamp shown in FIG. 3

DESCRIPTION OF THE PREFERRED EMBODIMENT

Referring now to the drawings, FIG. 1 shows tube clamp, shown generally at 10, which includes clamp housing 12, horizontal tube clips 14 and 16, and vertical tube clip 18. A second vertical tube clip is on the back side of clamp housing 12 and cannot be seen in FIG. 1. Horizontal tube clips 14 and 16 are removeably secured to the top surface 20 of the upper wing 22 of clamp housing 12. Extending downwardly from and secured to the lower surface of upper wing 22 is a first loop surface 24. (This loop surface 24 is part of a hook-loop fastener, such as a velcro fastener).

Extending through the lower wing 26 of clamp housing 12 is a threaded hole 28 which is adapted to receive threaded screw 30. Screw head 32 is affixed to the top of threaded screw 30

A second loop surface 34 is secured to the side of clamp housing 12. It should be noted that tubing clamp 10 may include more than one loop surface 34, or loop surface 34 may be placed anywhere on clamp housing 12, as desired, to function, e.g., as described below. Also, any or all of the loop surfaces, and the hook surfaces to be described below, may be changed to hook and loop surface, respectively, as desired, provided that when any two of these surfaces are brought together, as described below, a hook-loop fastener combination is obtained.

Strap 36 includes an outer hook surface 38 and an inner loop surface 40 and is shown in FIG. 1 as being secured to second loop surface 34.

Clamp housing 12 has a hole 42 extending down from the top of clamp housing 12. Hole 42 is adapted to receive and hold a writing instrument, e.g., pen 44, for the use and convenience of the medical practitioner using tubing clamp 10.

Referring to FIG. 2, bed rail clamp, shown generally at 46, includes a clamp hook surface 48 and two bed rail holders 50 and 52 which can be adapted to wrap around and become secured to a circular pole, such as a bed rail.

Tubing clamp 10 functions as follows. First, tubing clamp 10 is to be secured in place. Ordinarily, this is accomplished by positioning tubing clamp 10 so that a stationary object is between first loop surface 24 and screw head 32. Threaded screw 30 is then turned until tubing clamp 10 is secured to the stationary object. If this is not possible, e.g., because the stationary object is irregularly shaped, strap 36 is wrapped around the stationary object and then fastened to second loop surface 34, thereby securing tubing clamp 10 to the stationary object. If it is desired to secure tubing clamp 10 to a bed rail (or other similar object, bed rail holders 50 and 52 are wrapped around and secured to the bed rail and clamp hook surface 48 is brought into contact with first loop surface 24 to form, a hook-loop fastener and secure tubing clamp 10 to the bed rail.

In any event, once tubing clamp 10 is secured, it is ready for use. Tube clips 14, 16 and 10 are the quick connect-disconnect type clips is shown in FIG. 1, it is desired to have tubes 54 and 56 both run horizontally. Therefore, tube clips 14 and 16 are opened to receive tubes 54 and 56, respectively, and then closed so as to hold tubes 54 and 56, respectively. If tubes 54 and 56 are desired to run vertically (as shown in FIG. I) tube clip 18 and the unseen clip noted above are employed instead of tube clips 14 and 16 If a different diameter tube is to be held, tube clips 14, 16 and 18 may be removed and replaced by appropriately sized tube clips.

In the event strap 36 is not used to secure tube clamp 10 in place, it may be wrapped around the area of the patient, e.g., the patient's arm, where the tube or tubes enter the body to hold the tube or tubes in place. Thus strap 36 may be used in place of tape for patients who are allergic to tape. In addition, strap 36 may be used in this manner repeatedly whereas tape is costly and can only be used once.

Referring now to FIG. 3, pressure clamp, shown generally at 60, includes an upper arm 62, and a lower arm 64. Upper arm 62 is pivotally secured to lower arm 64 around pivot bolt 66. If desired, pivot bolt 66 might be easily placed through hole 68 in upper arm 62 to change the action of clamp 60 with a thumb screw adjustment.

Pivot-cradle element 70 is removably secured to lower arm 64 by wing nut 72. The position of cradle element can be readily adjusted to fit the neons of he particular application. In addition, wing nut 72 can be used to secure cradle element 70 through other holes (not shown in FIG. 3) in lower arm 64, thus giving additional adjustability to pressure clamp 60.

Flat head element 74 is removably secured to upper arm 62 by wing nut 76. Wing nut 76 can be used to secure flat head element 74 through hole 78, thereby providing still more increased flexibility to pressure clamp 60. Alternately, convex head element 80 (FIG. 4) may be employed in place of fiat head element 74. Convex head element 80 provides for substantially uniform pressure application over a relatively large area. Various sized heads (74 and 80) may be utilized for different applications.

Spring element 82 is shown in FIG. 3 as being connected to upper arm 62 through hole 83 and to lower arm 64 through hole 84. Spring element 82, enclosed in protective sheath 86 to protect the practitioner's hands is structured to provide variable tension, as desired. In addition, the tension applied by spring element 82 on pressure clamp 60 can be further adjusted by attaching spring element 12 to upper arm 62 through holes 86, 88 or 90, as desired.

Strap 92 is connected to upper D-ring 94 and lower D-ring 96 which are in turn, secured to upper arm 62 through hole 98 and to lower arm 64 through hole 100. Strap 92 includes opposing hook-loop surfaces which, when brought into contact with each other fasten to each other. The effective distance and pressure between upper arm 62 and lower arm 64 can be adjusted by adjusting the length of strap 92 by using the hook-loop fastening, mechanism noted above. In addition, upper and lower D-rings 94 and 96 can be secured to upper arm 62 and lower arm 64 through holes 102 and 104 and holes 106 and 108, respectively, as desired, to further adjust (control) the action of pressure clamp 60, nuts 110 and 112, associated with upper D-ring 94 and lower D-ring 96, respectively, may be used to change the point of attachment of such D-rings to upper arm 62 and lower arm 64, respectively.

Ring 114 attached to upper arm 62 through hole 116 is useful to store pressure clamp 60 when not in use.

As can be seen from the above description, pressure claim 60 is almost completely adjustable, in pressure and for extremity size, configuration and position on the individual as desired, to fit the needs of the particular patient and application involved.

Pressure clamp 60 is used as follows. The structure of pressure clamp 60 is adjusted, as desired (and as described above). The patient's extremity is comfortably placed in cradle element 70. Flat head element 74 is brought into contact with the extremity and the desired pressure is applied to the extremity. The effective length of strap 92 is adjusted to aid in maintaining this desired pressure. Pressure clamp 60 is removed by unfastening strap 92 and releasing spring element 82.

While this invention has been described with respect to various specific examples and embodiments, it is to be understood that the invention is not limited thereto and that it can be variously practiced within the scope of the following claims.

What is claimed is:

1. A clamp for applying pressure to a member comprising: a first frame having length; a second frame means movable secured to said first frame means; cradle means secured to said second frame means and being capable of acting to hold said member on which pressure is to be applied; and head means capable of being secured to said first frame means at different positions along the length of said first frame means and being capable of acting to contact said member being held by said cradle means whereby the desired pressure is applied to said member.

2. The clamp of claim 1 which further comprises bias means associated with both first and second frame means and being capable of acting to exert a force to maintain the desired pressure on said member.

3. The clamp of claim 2 wherein the force exerted by said bias means is adjustable, and the cradle means and head means are adjustably secured to the second and first frame means, respectively.

4. The clamp of claim 2 wherein said bias means comprises at lest one spring.

5. The clamp of claim 1 wherein both first and second frame means extend to first and second end means, respectively, and said clamp further comprises elongated strap means secured to both said first and second end means and being capable of acting to said in maintaining the desired pressure on said member.

6. The clamp of claim 5 wherein said elongated strap means has a first surface of hooks and an opposing second surface of loops, the effective length of said elongated strap means being adjustable by fastening the first surface to a different point on the second surface, as desired.

7. The clamp of claim 5 wherein said elongated strap means is capable of being secured to said first and second end means at any one of a plurality of points on said first and second end loans, respectively, as desired.

8. The clamp of claim 5 wherein the effective length of said strap means is adjustable to maintain said desired pressure on said member.

9. The clamp of claim 1 wherein said head means has a substantially flat surface capable of contacting said member, and rotates to properly contact the extremity surface regardless of shape, size or position.

10. The clamp of claim 1 wherein said head means has a substantially convex surface capable of contacting said member, also rotates to properly contact the extremity regardless of shape, size and position.

11. A clamp for applying pressure to a member comprising: a first frame means; a second frame means movably secured to said first frame means, said first and second frame means extending to first and second end means, respectively; cradle means secured to said second frame means and being capable of acting to hold said member on which pressure is to be applied; head means adjustably secured to said first frame means and being capable of acting to contact said member being held by said cradle means whereby the desired pressure is applied to said member; and elongated strap means at any one of a plurality of points on said first and second end means, respectively, as desired, and acting to aid in maintaining the desired pressure on said member.

* * * * *

UNITED STATES PATENT AND TRADEMARK OFFICE
CERTIFICATE OF CORRECTION

PATENT NO. : 4,821,720
DATED      : April 18, 1989
INVENTOR(S) : James D. Hajduch It is certified that error appears in the above—identified patent and that said Letters Patent is hereby corrected as shown below:

Column 1, line 51; delete "With" and insert -- with --.
Column 1, line 54; after "one" insert -- , --.
Column 1, line 67; delete "tho" and insert -- the --.
Column 2, line 13; delete "," (third occurrance).
Column 2, line 59; delete "surface" and insert -- surfaces --.
Column 3, line 33; after "16" insert -- . --.
Column 3, line 54; delete "neons of he" and insert
                   -- needs of the --.
Column 4, line 18; delete "," (first occurrance).
Column 4, line 51; after "first frame" insert -- means --.
Column 4, line 51; after "having" insert -- a --.
Column 4, line 52; delete "movable" and insert -- movably --.
Column 5, line 2; delete "lest" and insert -- least --.
Column 5, line 7; delete "said" and insert -- aid --.

Signed and Sealed this

Fourteenth Day of November, 1989

*Attest:*

JEFFREY M. SAMUELS

*Attesting Officer*   *Acting Commissioner of Patents and Trademarks*